United States Patent [19]

Triunfol

[11] Patent Number: 4,610,675
[45] Date of Patent: Sep. 9, 1986

[54] DEVICE FOR COLLECTING FLUID DISCHARGED FROM FEMALE ORGANS

[76] Inventor: David Triunfol, 2001 N. 72 Ct., Elmwood Park, Ill. 60635

[21] Appl. No.: 756,554

[22] Filed: Jul. 17, 1985

Related U.S. Application Data

[63] Continuation of Ser. No. 529,524, Sep. 6, 1983, abandoned.

[51] Int. Cl.⁴ .............................................. A61F 5/44
[52] U.S. Cl. ................................... 604/329; 4/144.3; 604/331
[58] Field of Search ............................ 604/329–331, 604/350, 317, 385, 359, 360; 128/132 A, 761; 4/144.1–144.4

[56] References Cited

U.S. PATENT DOCUMENTS

| | | | |
|---|---|---|---|
| 2,490,969 | 12/1949 | Kinyon | 604/329 |
| 3,556,102 | 1/1971 | Davis | 4/144.3 |
| 3,995,329 | 12/1976 | Williams | 604/329 |
| 4,270,539 | 6/1981 | Michaud | 4/144.3 |
| 4,281,655 | 8/1981 | Terauchi | 128/278 |
| 4,345,341 | 8/1982 | Saito | 4/144.3 |
| 4,484,917 | 11/1984 | Blackmon | 604/329 |
| 4,496,355 | 1/1985 | Hall et al. | 604/329 |

FOREIGN PATENT DOCUMENTS

| | | | |
|---|---|---|---|
| 794640 | 9/1968 | Canada | 604/329 |
| 2652088 | 5/1978 | Fed. Rep. of Germany | 604/360 |
| 996370 | 6/1965 | United Kingdom | 604/144.3 |

*Primary Examiner*—C. Fred Rosenbaum
*Assistant Examiner*—J. L. Kruter
*Attorney, Agent, or Firm*—Andrus, Sceales, Starke & Sawall

[57] ABSTRACT

A device for collecting fluid discharged from female organs. The device includes a flexible pad having an elongated central opening to register with the female pudendum. Ridges are formed on the inner surface of the pad, on either side of the opening, and are adapted to exert pressure on the area bordering the labia majora to urge the labia to an open condition. Corresponding edges of the ridges at one end of the pad are spaced apart to provide a gap to receive the clitoris, while corresponding ends of the ridges at the opposite end of the pad are connected together at a junction which is adapted to engage the navicular fossa. In one form of the invention, in which the device is utilized to collect urine, a bag or receptacle is connected to the opening in the pad and the lower end of the receptacle defines an outlet that is connected through a conduit to a vacuum pump. A liquid sensor is located at the outlet and senses the presence of urine to start operation of the pump and remove the urine from the receptacle. When used as a sanitary napkin, an absorbent material is located within the pad and communicates with the central opening so that menstrual fluid can freely flow into the absorbent material and be absorbed therein.

7 Claims, 5 Drawing Figures

DEVICE FOR COLLECTING FLUID DISCHARGED FROM FEMALE ORGANS

This is a continuation of application Ser. No. 06/529,524, filed Sept. 6, 1983 now abandoned.

BACKGROUND OF THE INVENTION

Hospitals and health care facilities are continuously faced with the problem of urine incontinence. The most common method of collecting urine in the incontinent patient, is the use of in-dwelling bladder catheters. However, in-dwelling catheters present serious problems as they are a frequent source of infection. For example, the article "Mortality Associated With Nosocomial Urinary-Tract Infection", Platt et al, New England Journal of Medicine, Sept. 9, 1982, states that there are approximately 7.5 million persons who are catheterized eacy year in the acute-care hospitals in the United States and it is estimated that 390,000 mortalities occur each year associated with catheter-related infection.

In addition to being a source of infection, the accidental or intentional removal of the in-dwelling catheter by the patient can result in damage to the urethra. With the use of an in-dwelling catheter, a bulb on the distal end of the catheter is expanded after insertion which tends to press and irritate the urethra. Because of the irritation, patients frequently will attempt to remove the catheter with the result that the expanded end can cause tears or ruptures to the urethra, a problem which frequently can only be corrected through surgery.

Because of the problems with the in-dwelling catheter, there has been a need for an external urine collecting device. U.S. Pat. No. 4,281,655 describes a urine collecting device adapted primarily for a male patient and including a semi-spherical urine receiving unit which is positioned around the patient's organs and is adapted to seal against the body through use of a rubber tube bordering the receiving unit. In accordance with the aforementioned patent, when urine is excreted. it is sensed by a sensor which actuates a vacuum pump to withdraw the urine from the receiving unit. The device shown in the aforementioned patent is not contoured to precisely seal against the body and cannot be adapted to female patients, or male patients.

Both sanitary napkins and tampons are regularly used to collect the flow of menstrual fluid, but both of these devices tend to impede the discharge of menstrual fluid and, as such, increase the risk of infection. A tampon retains the menstrual fluid in the vagina, while the conventional sanitary napkin, when attached to the body, will tend to close the labia to restrict or inhibit flow of menstrual fluid to the napkin.

SUMMARY OF THE INVENTION

The invention is directed to a device for collecting fluid discharged from female organs, and in particular can be used to collect urine and/or menstrual fluid.

The device consists of a curved, flexible pad having an elongated central opening which extends in a front-to-rear direction and is adapted to register with the female pudendum. A pair of longitudinal ridges are formed on the inner surface of the pad, straddling the opening, and are disposed to exert pressure on the area bordering the labia majora to urge the labia to an open condition. The corresponding forward ends of the ridges are spaced apart to provide a gap to receive the clitoris, while the corresponding rearward ends of the ridges are connected together at a junction which is positioned to engage the navicular fossa. When attached to the body, the pressure exerted by the ridges acts to maintain the labia in an open condition to permit free discharge of fluid from the vestibule.

When used to collect urine, a flexible receptacle is attached to the outer surface of the pad and communicates with the opening so that urine will flow through the opening into the receptacle. The lower end of the receptacle defines an outlet that is connected by a conduit to a vacuum pump and a liquid sensor is located at the outlet. When urine flows to the outlet, the sensor will be energized to activate the vacuum pump to remove the urine from the receptacle. When the flow of urine ceases, the sensor will discontinue operation of the vacuum pump.

When the device is used to collect menstrual fluid, an absorbent material is located within the pad and communicates with the opening so that the menstrual fluid will be collected in the absorbent material.

The device of the invention is configured to apply pressure to the area bordering the labia majora to urge the labia to an open condition to thereby obtain free flow of fluid into the pad. As the labia are maintained in an open condition there is no tendency to retain fluid in the body cavities and this reduces the possibility of infection.

The device is flexible and, when attached, is contoured to fit the body to minimize leakage of fluids. As the device is applied externally, it is comfortable and provides greater mobility for the patient.

Other objects and advantages will appear in the course of the following description.

DESCRIPTION OF THE DRAWINGS

The drawings illustrate the best mode presently contemplated of carrying out the invention.

In the drawings.

DESCRIPTION OF THE ILLUSTRATED EMBODIMENT

Figure 1:
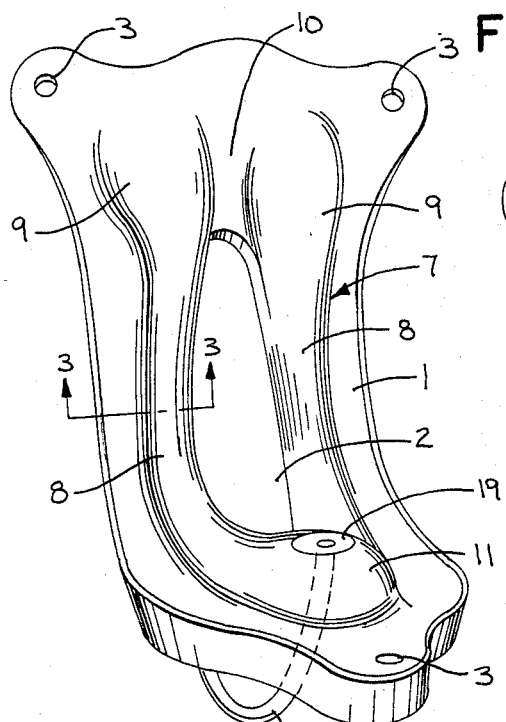
FIG. 1 is a perspective view of the device of the invention as used to collect urine.
Figure 2:
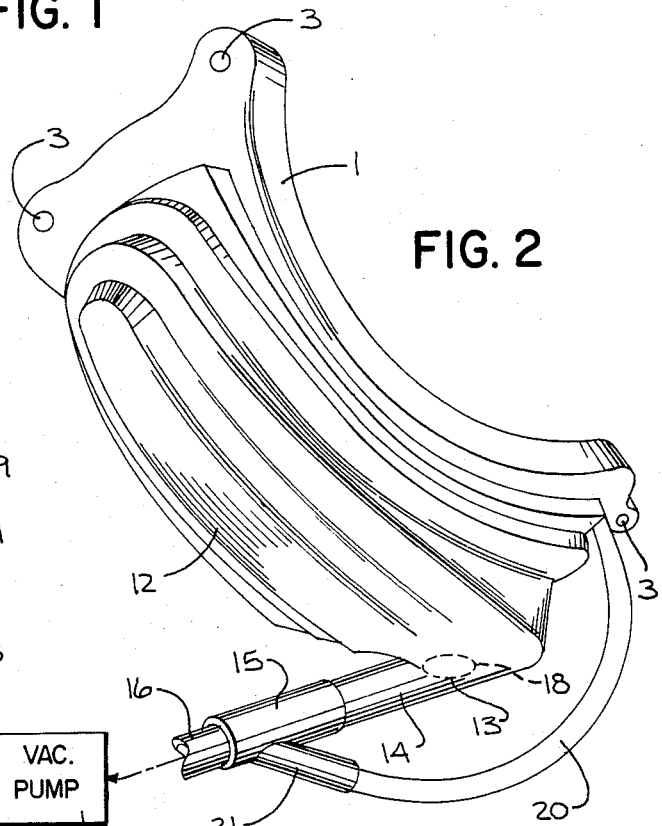
FIG. 2 is a perspective view of the bottom of the device shown in FIG. 1.

FIGS. 1 and 2 illustrate the device of the invention as used to collect urine from a female patient. The device includes a longitudinally extending curved flexible pad 1, having an elongated opening 2 which extends in a front-to-rear direction. The ends of the pad can be provided with a series of holes 3 which receive a strap, not shown, to connect the pad top the body.

Figure 3:
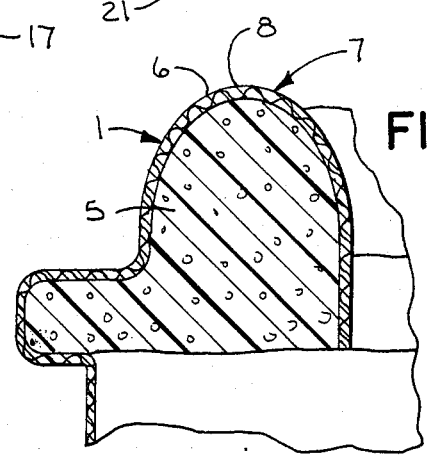
FIG. 3 is a section taken along line 3—3

As shown in FIG. 3, pad 1 is composed of a core 5 formed of a flexible material, such as polyurethane, and an outer impervious cover 6 which can be formed of a material such as polyethylene.

In accordance with the invention, the inner surface of the pad 1 is formed with a generally U-shaped ridge 7 which includes a pair of upraised converging side or labial ridges 8 located on either side of central opening 2. As shown in FIG. 1, the forward ends of the labial ridges project past the corresponding ends of opening 2 and terminate in clitoral ridges 9. The clitoral ridges 9 are spaced apart to provide a gap 10 that receives the clitoris.

The rearward ends of the labial or side ridges 8 are joined together by a perineal ridge 11 which has a slightly greater height than the labial ridges. In use, the perineal ridge 11 is adapted to engage and bear against the navicular fossa.

When pad 1 is applied to the body, the labial ridges 8 apply pressure to the area bordering the labia majora to urge the labia to an open condition, so that the labia do not restrict flow of urine into the opening 2.

Attached to the outer surface of pad 1 is a receptacle 12 which can be formed of a transparent plastic film, such as polyethylene. The lower end of receptacle 12 defines an outlet 13 which is connected to nipple 14. Connector 15 connects nipple 14 with a tube 16 that is connected to a source of vacuum, such as a conventional vacuum pump, shown schematically by 17.

Located at the outlet 13 is a conventional liquid sensor 18 which senses the presence of liquid. When the presence of liquid is sensed by sensor 18, the sensor generates an electrical signal which operates through a conventional electrical circuit to start operation of the vacuum pump 17 to withdraw the urine from the receptacle. After the urine has been withdrawn from the receptacle, the sensor 18 will act to discontinue operation of the vacuum pump 17.

In certain instances it may be desirable to incorporate a second liquid sensor with the device. In this regard, a sensor 19 can be located on the inner surface of pad 1 at the rearward end of opening 2 at the perineal ridge 11. Sensor 19 is connected by tube 20, which extends in sealed relation within an opening in pad 1, to an arm 21 on connector 15. If there is any leakage of urine to the area of the navicular fossa, sensor 19 will sense the presence of the urine to operate the vacuum pump 17 to withdraw the urine from this area.

Figure 4:
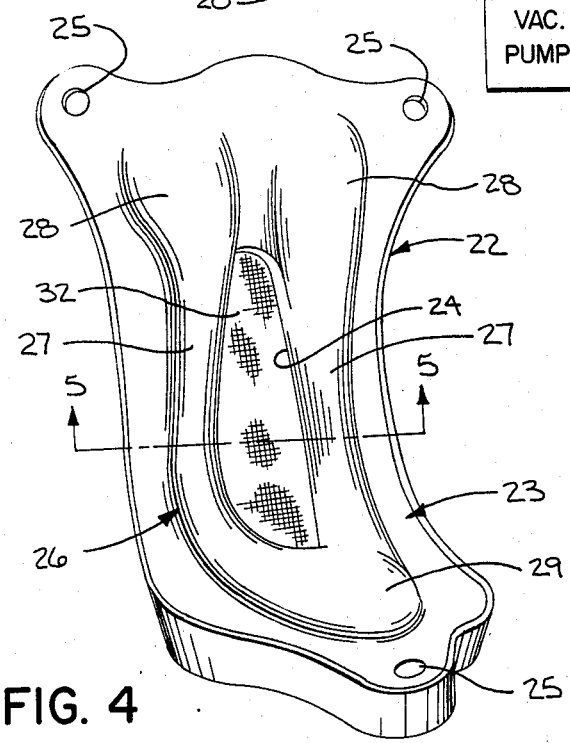
FIG. 4 is a perspective view of the device as used as a sanitary napkin.
Figure 5:
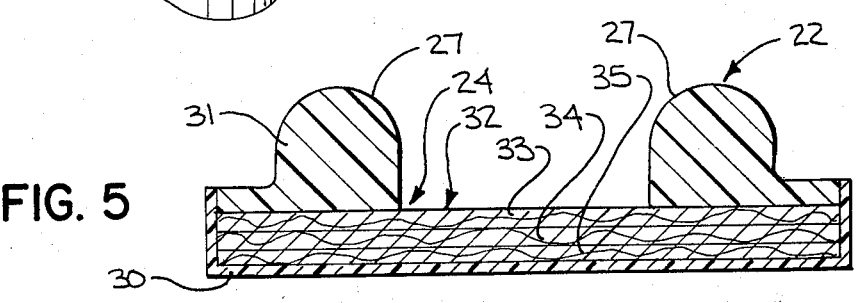
FIG. 5 is a section taken along line 5—5 of FIG. 4.

FIGS. 4 and 5 illustrate a second form of the invention in which the device is utilized as a sanitary napkin 22 to collect menstrual fluid. In this embodiment, the device includes a flexible pad 23, similar to pad 1, and pad 23 is provided with an elongated central opening or recess 24. Holes 25 can be provided in the pad to receive straps, not shown, to attach the pad to the body in a manner so that the longitudinal axis of opening 24 extends in a front-to-rear direction.

As the the case of the first embodiment, the inner surface of pad 23 is formed with a generally U-shaped ridge 26, similar to ridge 7, and the ridge is composed of a pair of side or labial ridges 27 which terminate at the forward end in clitoral ridges 28. Ridges 28 are spaced apart to provide a gap that receives the clitorus.

The rearward ends of the labial ridges 27 are connected together by a perineal ridge 29 which has a slightly greater height than labial ridges. As previously described, when the pad 22 is applied to the body, the labial ridges 27 will exert pressure on the area bordering the labia majora causing the labia to move to an open condition and thereby permit free flow of menstrual fluid to the pad 22.

The construction of the pad 22 is best illustrated in FIG. 5 and is composed of an impervious backing layer 30, composed of appropriate plastic or other material, which extends over the rear or back surface, as well as over the side edges of the pad.

The body 31 of pad 22, including the ridge 26 is formed from a flexible material, such as polyurethane, and an absorbent core 32 is located between the backing layer 30 and the body 31 and covers substantially the full area of pad 22. The core 32 is preferably formed of two layers of absorbent fibrous material 33 and 34 which are located on either side of an intermediate layer 35 of fibrous material which may be impregnated with an antiseptic material such as a bacteriacide or deodorant. As shown in FIG. 5, the absorbent core is exposed through the opening 24 so that the menstrual fluid flowing through the opening will be absorbed in the core 32.

In the device of the invention, the ridges 7 and 26 are configured to apply pressure to the area bordering the labia majora to urge and maintain the labia in an open condition so that free flow of fluid is attained. As there is no restriction to the flow of fluid, there is no tendency to retain the fluid in the body cavities and this thereby reduces the possibility of infection.

The device, when used to collect urine, is attached exteriorly and, as such, is more comfortable and provides greater mobility for the patient than the conventional in-dwelling catheters as used in the past. Furthermore, any discharged urine is automatically removed to prevent the accumulation of urine either in the receptacle or in the area of the navicular fossa. For the ambulatory patient, the pad 1 may be connected to a urine collecting bag secured by a belt to the thigh of the patient.

Various modes of carrying out the invention are contemplated as being within the scope of the following claims particularly pointing out and distinctly claiming the subject matter which is regarded as the invention.

I claim:

1. A device for collecting fluids from a female patient's genitals, comprising a flexible pad having a generally flat contour prior to application to the urogenital area of a female body and when applied to the external portions of the urogenital area assuming a curvlinear shape, said pad having a longitudinal central opening and having an inner surface to be in contact with said external portions and having an outer surface, said pad further having a pair of longitudinal extending side ridge means on said inner surface straddling the opening for exerting pressure on the external portion of the urogenital area bordering the labia majora to urge and hold the labia majora in an open condition, corresponding ends of said ridge means being laterally spaced and non-connecting and together with said inner surface forming an open gap to receive the clitoris, and opposite ends of the ridge means being connected together at an upraised junction means forming a perineal ridge disposed to engage the navicular fossa, and collecting means connected to the outer surface of the pad for collecting fluid discharged into said opening from the female genitals.

2. The device of claim 1, wherein said collecting means comprises an absorbent material disposed across said opening, said device being adapted to collect menstrual fluid which is absorbed in said absorbent material.

3. The device of claim 1, wherein said collecting means includes a receptacle connected to said opening, fluid passing through said opening being collected in said receptacle.

4. The device of claim 3, and including a source of vacuum, conduit means connecting the receptacle to the source of vacuum, and liquid sensing means disposed within the receptacle and operably connected to said source of vacuum, said liquid sensing means sensing the presence of liquid in the receptacle and acting to operate the source of vacuum to withdraw said liquid from said receptacle.

5. The device of claim 1, wherein said junction ridge means has a height greater than the height of said side ridge means.

6. The device of claim 1, and including means connected to the pad for attaching the pad to a female body.

7. A device for collecting urine from a female patient, comprising a generally longitudinally extending curved flexible pad adapted to be attached externally to a female body and having an elongated central opening extending in a front-to-rear direction and adapted to register with the female pudendum, a pair of side upraised converging ridges disposed on the inner surface of the pad and straddling said opening, said side ridges disposed to exert pressure on an area bordering the labia majora to urge the labia in an open condition, the forward ends of the ridges being spaced apart to provide a gap means between the side ridges to receive the clitoris and the rear ends of the ridges being connected together to form a perineal upraised ridge junction means, said ridge junction means disposed to engage the navicular fossa, a receptacle communicating with said opening and having an outlet at its lower end, a vacuum pump, conduit means connecting the vacuum pump with said outlet, liquid sensing means sensing the presence of urine at said outlet and operably connected to said vacuum pump to operate said vacuum pump and withdraw the urine from said receptacle, second conduit means connecting the pad at a location adjacent to said ridge junction means to the vacuum pump, and second liquid sensing means disposed on the inner surface of said pad adjacent said ridge junction means and operably connected to said vacuum pump, said second sensing means sensing the presence of urine at said ridge junction means and acting to operate said vacuum pump to remove urine from said location.

* * * * *